United States Patent
Sakaguchi et al.

(10) Patent No.: US 9,114,045 B2
(45) Date of Patent: Aug. 25, 2015

(54) ABSORBENT ARTICLE USING HOOK-AND-LOOP FASTENER

(75) Inventors: Satoru Sakaguchi, Kagawa (JP); Tomomi Oku, Kagawa (JP); Hideki Matsushima, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 839 days.

(21) Appl. No.: 13/394,379

(22) PCT Filed: Sep. 9, 2010

(86) PCT No.: PCT/JP2010/005527
§ 371 (c)(1),
(2), (4) Date: May 3, 2012

(87) PCT Pub. No.: WO2011/030550
PCT Pub. Date: Mar. 17, 2011

(65) Prior Publication Data
US 2012/0245550 A1  Sep. 27, 2012

(30) Foreign Application Priority Data
Sep. 9, 2009 (JP) ................................. 2009-208695

(51) Int. Cl.
  *A61F 13/15* (2006.01)
  *A61F 13/82* (2006.01)
  *A61F 13/62* (2006.01)

(52) U.S. Cl.
CPC .............. *A61F 13/62* (2013.01); *A61F 13/627* (2013.01); *A61F 13/622* (2013.01); *A61F 13/625* (2013.01)

(58) Field of Classification Search
CPC ....... A61F 13/82; A61F 13/62; A61F 13/622; A61F 13/625; A61F 13/627
USPC .......................... 604/391, 386, 387, 396, 394
See application file for complete search history.

(56) References Cited

U.S. PATENT DOCUMENTS

| 6,637,079 B1 | 10/2003 | Goulait et al. |
| 6,770,065 B1 | 8/2004 | Sasaki et al. |
| 2008/0208157 A1 | 8/2008 | Horn et al. |

FOREIGN PATENT DOCUMENTS

| JP | 6033359 A | 2/1994 |
| JP | 11061624 A | 3/1999 |

(Continued)

OTHER PUBLICATIONS

International Search Report and Written Opinion for PCT/JP2010/005527 dated Dec. 21, 2010.

(Continued)

*Primary Examiner* — Jacqueline Stephens
(74) *Attorney, Agent, or Firm* — Lowe Hauptman & Ham, LLP

(57) ABSTRACT

In a hook-and-loop fastener, the female member includes a plurality of lines of fiber dense portions in which the fibrous material has a high basis weight, a plurality of lines of fiber sparse portions provided between the plurality of lines of fiber dense portions, the fibrous material in the fiber sparse portions having a basis weight lower than that in the fiber dense portions, and pressed portions intersecting the plurality of lines of fiber dense portions and the plurality of lines of fiber sparse portions. Further, since the rib portions are pressed by the pressed portions obtained by the embossing process, the rib portions change shape from lines where the rib portions intersect the pressed portions, and curve toward the peeling direction shown by arrow a to be a convex shape.

15 Claims, 11 Drawing Sheets

(56) References Cited

FOREIGN PATENT DOCUMENTS

| | | | |
|---|---|---|---|
| JP | 11152669 A | 6/1999 | |
| JP | 11302963 A | 11/1999 | |
| JP | 11335960 A | 12/1999 | |
| JP | 2007268219 A | 10/2007 | |

OTHER PUBLICATIONS

Extended European Search Report issued Mar. 19, 2014 corresponds to European patent application No. 10815150.7.

(a)

(b)

ABSORBENT ARTICLE USING HOOK-AND-LOOP FASTENER

RELATED APPLICATIONS

The present application is National Phase of International Application Number PCT/JP2010/005527, filed Sep. 9, 2010, and claims priority from Japanese Application Number 2009-208695, filed Sep. 9, 2009.

TECHNICAL FIELD

The disclosure relates to an absorbent article using a hook-and-loop fastener which includes a female member and a male member that engages with the female member.

BACKGROUND ART

An absorbent article such as a paper diaper is designed to be opened by using a hook-and-loop fastener so that the absorbent article can be attached and detached to and from a human body. The hook-and-loop fastener includes a male member and a female member that are joined to and separated from each other by engagement and disengagement therebetween. The male member is formed to have an engagement face including a group of multiple protrusions (hooks), and the female member is made of a nonwoven fabric or a knitted cloth with which the group of protrusions can engage. Patent Literatures 1 to 3 each disclose a conventional example of the female member in the hook-and-loop fastener.

Patent Literature 1 describes a female member made from an embossed air-through nonwoven fabric whose main fibers are 30 to 100 mm long. The nonwoven fabric is embossed over the full width thereof with a pattern which intersects an MD direction, so that the embossed nonwoven fabric may be stretched out at elongation percentage of 75% or less than that before the emboss process when weighted in a CD direction by 2N/25 mm, and have a thickness of 0.4 mm or more. The fibers constituting the air-through nonwoven fabric form a layer structure in which the fibers are basically two-dimensionally arranged in layers and are fusion-bonded to one another. In other words, the emboss process is performed in a pattern that intersects the MD direction in which a number of fibers are arranged. By the emboss process, the fiber layers are fused and integrated to strengthen the connection between the fibers and to make the fibers less fluffy.

Patent Literature 2 describes a female member formed as follows. Specifically, a spunbonded nonwoven fabric is placed on and integrated with a heat-shrinkable fabric web, and thereafter the fiber web is contracted by thermal processing to form 2 to 40 wrinkles per $cm^2$ in the spunbonded nonwoven fabric, the wrinkles each having a depth of 0.2 mm to 3 mm. In the spunbonded nonwoven fabric, endless fibers two-dimensionally arranged are securely fused by thermal embossing or the like. Accordingly, the spunbonded nonwoven fabric has a characteristic of being unlikely to be fluffy. When the heat-shrinkable fiber web integrated with a lower layer side of the spunbonded nonwoven fabric is thermally contracted, a number of wrinkles are formed in the spunbonded nonwoven fabric, and the wrinkles allow the female member to engage with the male member.

Patent document 3 discloses that loops of a fiber bundle are formed in a heat-nonshrinkable fiber layer in a perforated nonwoven fabric in the following manner. Specifically, the perforated nonwoven fabric is obtained by stacking the heat-nonshrinkable fiber layer on a heat-shrinkable fiber layer, and then by ejecting a high-pressure fluid onto the layered body to interlace the fibers with one another while re-arranging the fibers. Thereafter, the perforated nonwoven fabric is heated to contract the heat shrinkable fiber layer and thereby to form the loops of a fiber bundle in the heat-nonshrinkable fiber layer. With such processes, curled objects projecting in random directions are formed.

CITATION LIST

Patent Literature

Patent Literature 1: Japanese Patent Application Publication No. Hei 11-335960
Patent Literature 2: Japanese Patent Application Publication No. Hei 6-33359
Patent Literature 3: Japanese Patent Application Publication No. Hei 11-152669

SUMMARY OF INVENTION

In Patent Document 1, connections of fibers are spread out in all directions on a plane of a nonwoven fabric by thermal fusion bonding, and the fibers are further strongly integrated by the emboss process. Accordingly, the nonwoven fabric has a large engagement strength with a male member and is less fluffy. On the other hand, the nonwoven loses its elasticity in a release direction of the engagement. For this reason, when a hook-and-loop fastener is deformed while the diaper or the like is being worn, or receives an instantaneous impulsive force for peeling, the female member easily comes off from the male member due to the lack of engagement persistence.

The female member of Patent Literature 2 shows similar behaviors to those of Patent Literature 1, and thus has similar problems.

Patent Literature 3 does not have such problems as Patent Literatures 1 and 2 have, because loops of a fiber bundle are formed and because fibers of an entire nonwoven fabric are loosely connected by fiber interlacing. However, Patent Literature 3 has a problem that the nonwoven fabric, in which the fibers are loosely connected by fiber interlacing, becomes fluffy because fibers easily fall off when the male member is disengaged. However, if fiber interlacing is intensified to address this problem, the entire nonwoven fabric becomes too tight to generate loops of a fiber bundle by thermal contraction. This makes it difficult for the male member to be caught by the female member.

In this regard, an objective of the present invention is to provide an absorbent article using a hook-and-loop fastener which does not allow a male member to easily come off even if a hook-and-loop portion is deformed or receives an instantaneous impulsive peeling force, and which also does not allow a fibrous material to fall off and thus does not become fluffy after the male member is peeled off.

To solve the above-described problem, the present invention has the following aspects. An aspect of the present invention is summarized as an absorbent article formed of an outer member having a front waistline portion, a back waistline portion, and a crotch portion and of an absorber provided integrally to the crotch portion, the absorbent article comprising a hook-and-loop fastener that includes a male member which is provided to any one of the front waistline portion and the back waistline portion and which has an engagement surface formed of a group of a plurality of protrusions and a female member which is formed of a fibrous material and is configured to engage with the male member. The female member includes a plurality of lines of fiber dense portions in which the fibrous material has a high basis weight, a plurality of lines of fiber sparse portions provided between the plurality of lines of fiber dense portions, the fibrous material in the fiber sparse portions having a basis weight lower than that in the fiber dense portions, and pressed portions intersecting the plurality of lines of fiber dense portions and the plurality of lines of fiber sparse portions.

The aspects of the present invention described above may be arranged in at least the following items:

(i) A hook-and-loop fastener including: a male member which has an engagement surface formed of a plurality of protrusions; and a female member which is formed of a fibrous material and is configured to engage with the male member, wherein the female member includes: a plurality of lines of fiber dense portions in which the fibrous material has a high basis weight; a plurality of lines of fiber sparse portions provided between the plurality of lines of fiber dense portions, the fibrous material in the fiber sparse portions having a basis weight lower than that in the fiber dense portions; and pressed portions intersecting the plurality of lines of fiber dense portions and the plurality of lines of fiber sparse portions.

Additionally, one or more of the following embodiments are provided in accordance with further aspects:

(ii) the fiber dense portions may comprise ribs and the fiber sparse portions may comprise grooves, and the fibrous material may have a greater thickness at the fiber dense portions than at the fiber sparse portions.

(iii) the fiber dense portions may be wider than the fiber sparse portions.

(iv) the fiber sparse portions and the fiber dense portion may be arranged alternately to one another. The fiber dense portions and the fiber sparse portions may be continuous. The fiber sparce portions and the fiber dense portions preferably extend in the MD direction of the fibrous material.

(v) opening portions, which penetrate from the front to the back of the female member in the thickness direction may be provided in the fiber sparse portions.

(vi) the pressed portions may comprise embossed lines. The pressed portions may be continuous.

(vii) the pressed portions may be orthogonal or oblique to the lines of fiber sparse and fiber dense portions.

(viii) the pressed portions may be narrower than the lines of fiber sparse and fiber dense portions. The pressed portions may be less than 1 mm wide.

(ix) the basis weight of the fibrous material may be 15 to 100 g/m$^2$.

(x) the pitch between adjacent pairs of ribs may be 1.5 to 15 mm, the width of each rib may be 1 to 10 mm, the width of each groove may be 0.5 to 5 mm and a height of each rib may be 0.2 to 5 mm.

(xi) An absorbent article formed of an outer member having a front waistline portion, a back waistline portion, and a crotch portion and of an absorber provided integrally to the crotch portion, the absorbent article comprising a fastener as recited in any of the aspects above, wherein the male member of the fastener is provided on any one of the front waistline portion and the back waistline portion.

(xii) the female member may be rectangular and provided on the front waistline portion, and the pressed portions may be formed across the length of the female member or in only both lengthwise edge portions of the female member.

(xiii) a marker indicating a center part of the female member may be formed in a center portion of the female member, the center portion being other than both the lengthwise edge portions.

(xiv) the female member may comprises a topsheet of the absorbent article.

(xv) a first bonding material, which may be applied in strips, may be placed between the absorber and the female member, which female member comprises the topsheet, the first bonding material bonding the topsheet to the absorber, a second bonding material, which may be applied in strips, may be placed between a back side of the female member, the back side being opposite to a side where the fiber dense portions are formed, and a portion of the absorbent article lying outside the absorber, the second bonding material bonding the female member to the portion of the absorbent article lying outside the absorbent article, and an application width of the strips of the first bonding material may be smaller than a width of each of the fiber dense portions formed on the topsheet, and may be smaller than an application width of the strips of the second bonding material.

(xvi) the strips of the second bonding material may be applied on a back side of the female member in regions that correspond to the lines of fiber dense portions, and may be 50% or more of a corresponding width of each of the fiber dense portions.

(xvii) the fiber dense portions and the fiber sparse portions may each extend in a longitudinal direction of the absorbent article. That is, the lines of the fiber dense and fiber sparse portions may be aligned with the longitudinal direction of the absorbent article. The fiber dense and the fiber sparse portions may extend continuously or discontinuously.

DESCRIPTION OF THE EMBODIMENT

Embodiments of a hook-and-loop fastener used in an absorbent article according to the present invention will be described with reference to the drawings. Note that, in the following description of the drawings, same or similar reference signs denote same or similar elements and portions. In addition, it should be noted that the drawings are schematic and ratios of dimensions and the like are different from actual ones.

Therefore, specific dimensions and the like should be determined in consideration of the following description. Moreover, the drawings also include portions having different dimensional relationships and ratios from each other. In the following description, configurations having a similar advantageous effect are denoted by the same reference sign, and are not described repeatedly in detail.

Figure 1:
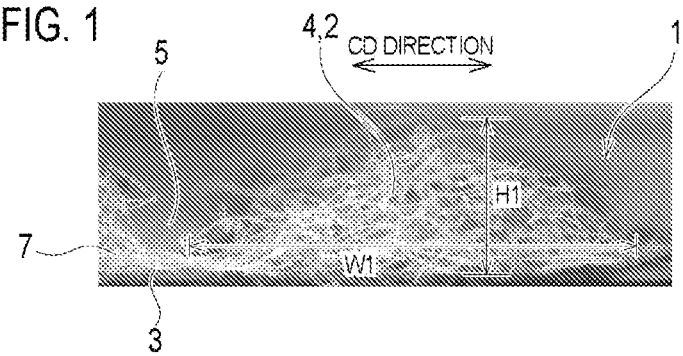
FIG. 1 is a cross-sectional view showing a female member of an embodiment of the present invention.

FIGS. 1 and 2 show a female member 1 of a hook-and-loop fastener. The female member 1 is an air-through nonwoven fabric made of many fibrous materials, and is formed by fusing the fibrous materials with one another by hot air. As FIG. 1 shows, the female member 1 includes fiber dense portions 2 and fiber sparse portions 3.

The fiber dense portions 2 are where the fibrous material has a high basis weight, whereas the fiber sparse portions 3 are where the fibrous materials have a low basis weight. Here, the basis weight is the weight (amount) of the fibrous material has per unit area, and is represented by a unit of $g/m^2$, for example. The fiber dense portions 2 and the fiber sparse portions 3 are each shaped as a strip extending in an MD direction (a direction in which the absorbent article is fed when manufactured). Further, the fiber dense portions 2 and the fiber sparse portions 3 are arranged in multiple lines in a CD direction (a direction orthogonal to the direction in which the absorbent article is fed when manufactured). The lines of the fiber sparse portions 3 are positioned between the lines of the fiber dense portions 2. In other words, the fiber dense portions 2 and the fiber sparse portions 3 are arranged alternately in the CD direction. Note that such alternate arrangement of the fiber dense portions 2 and the fiber sparse portions 3 includes arrangement of a fiber dense portion, a fiber sparse portion, a fiber sparse portion, and a fiber dense portion, or arrangement of a fiber sparse portion, a fiber dense portion, a fiber dense portion, and a fiber sparse portion.

As will be described later, the fiber dense portions 2 are formed by laminating fibrous materials by hot air, and form convex rib portions 4. The fiber sparse portions 3 are where the fibrous materials are removed by hot air, and form concave groove portions 5. The rib portions 4 and the groove portions 5 are each continuous in the MD direction, and are arranged alternately in the CD direction. Fibrous materials constituting one rib portion 4 form a fiber aggregate in that rib portion 4. Moreover, most of the fibrous materials constituting one rib portion 4 are independent from an adjacent rib portion 4. Further, the rib portions 4 are formed by laminating fibrous materials on a base layer portion 7 which is formed by the thickness of the fibrous materials under the groove portion 5. The volume of the fibrous materials laminated on the base layer portion 7 is equal to that of the fibrous materials which used to be in the groove portions 5. In other words, the fibrous materials removed by hot air are laminated on both sides of each groove portion 5 to form the fiber sparse portion 3 under the groove portion 5, and thus the fiber dense portions 2, namely the rib portions 4, are formed.

Figure 2A:
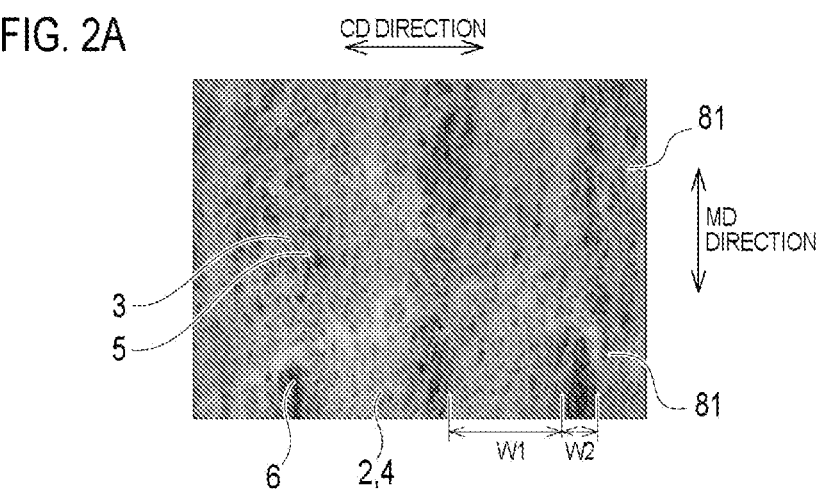
FIG. 2A is a plane view showing a top surface of the female member of the embodiment.
Figure 2B:
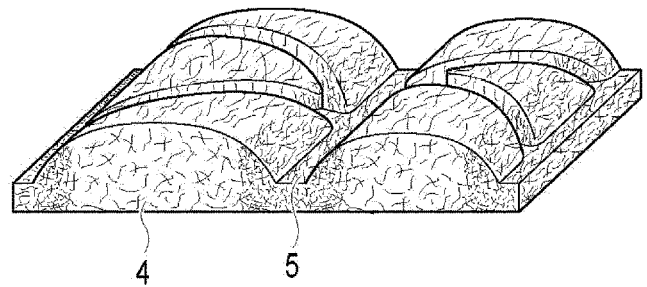
FIG. 2B is perspective view showing the female member of the embodiment.

As FIGS. 2A and 2B show, the female member 1 of the hook-and-loop fastener includes pressed portions 81 that intersect the multiple lines of the fiber dense portions 2 (the rib portions 4) and the multiple lines of the fiber sparse portions 3 (the groove portions 5). In the present embodiment, the pressed portions 81 are formed by thermal fusion bonding using embossing rolls. Note that the formation method is not limited to the thermal fusion bonding as long as the pressed portions 81 are formed thinner than other areas. The pressed portions 81 may be formed by a pressing process that involves no heating.

Note that, as FIGS. 1, 2A and 2B show, some of the fibrous materials of one rib portion 4 are connected to an adjacent rib portion 4 at bottom portions of the rib portions 4 (the base layer portion 7). Such connection allows the female member 1 to keep its form as a nonwoven fabric sheet.

Figure 3:
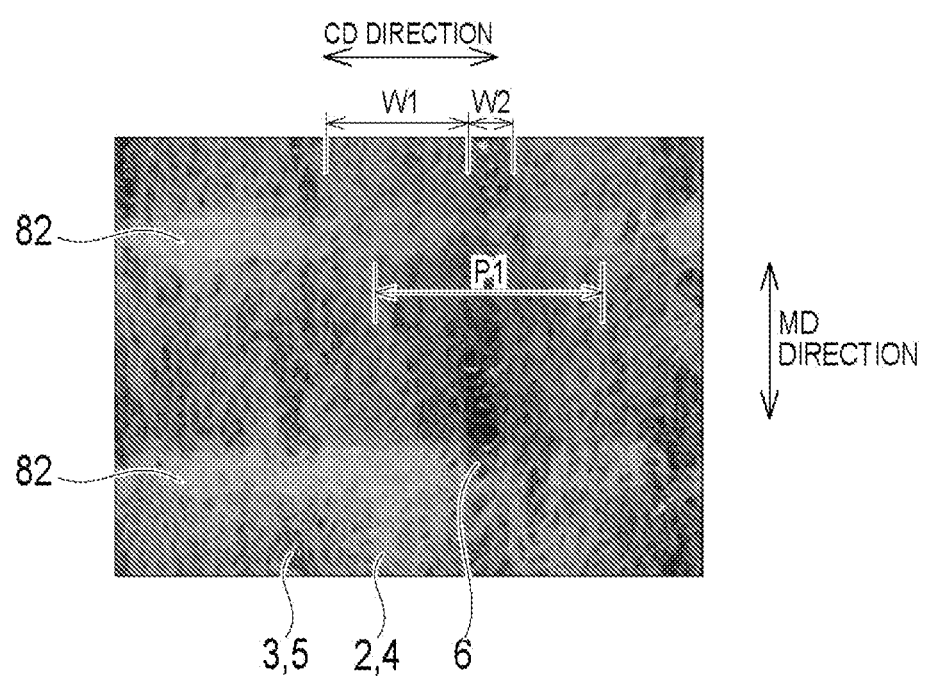
FIG. 3 is a plane view showing a top surface of a female member of another embodiment.

As FIGS. 2A and 2B show, opening portions 6 are formed in the groove portions 5 (the fiber sparse portions 3). The opening portions 6 are formed penetrating from the front to the back of the female member 1. The opening portions 6 are formed by removing fibrous materials by hot air. By forming the opening portions 6 in the groove portions 5, more fibrous materials can be moved toward the rib portions 4 by the amount of the opening portions 6. Thereby, the basis weight of the rib portions 4 can be increased. As a result, an engagement strength between the rib portions 4 and a male member (not shown) can be large, allowing stable engagement with the male member. Further, as FIG. 3 shows, fibrous materials near the opening portions 6 tend to be oriented in the CD direction. Accordingly, the sheet has an improved capability of stretching in the CD direction. Note that the opening portions 6 do not necessarily have to be formed.

In the present embodiment, as FIG. 1 shows, the rib portions 4 are formed on a top side of the female member 1 and a back side thereof is flat. Alternatively, the rib portions 4 may be formed on both top and back sides.

In addition, in the above embodiment example, the rib portions 4 are formed by removing fibrous materials by hot air and laminating those fibrous materials on both sides of each groove portion 5. Alternatively, the groove portions 5 may be formed by giving dips and bumps on a surface using a comb-like tool to remove fibrous materials, and the rib portions 4 may be formed by moving the fibrous materials thus removed from the groove portions 5 to both sides of each groove portion 5.

FIG. 3 shows another embodiment of the female member 1 of the hook-and-loop fastener. In the female member 1 of the hook-and-loop fastener shown in FIG. 3, pressed portions 82 are orthogonal to the rib portions 4 and the groove portions 5.

Next, a description is given of conditions for the female member 1, such as dimensions and materials.

The basis weight of the entire nonwoven fabric constituting the female member 1 is preferably 15 to 100 $g/m^2$, or more preferably, 20 to 40 $g/m^2$. A basis weight of at least 15 $g/m^2$, is preferred to ensure sufficient strength in the CD direction of fibrous material for the groove portions 5. A basis weight of 100 $g/m^2$ or less is preferred to ensure that costs are not increased unnecessarily.

A pitch P1 between each adjacent pair of the rib portions 4 (see FIGS. 2 and 3) is preferably 1.5 mm to 15 mm, or more preferably, 3 to 8 mm. A pitch P1 of at least 1.5 mm, is preferred to ensure that the rib portions 4 may be formed evenly within the above-described basis weight. This is because the rib portions 4 are formed by removing fibers. A pitch P1 of 15 mm or less is preferred to ensure that the rib portions are formed having a sufficient height and width to ensure smooth engagement with the male member and a suitable area for engagement with the male member.

A width W1 of each rib portion 4 is preferably 1 mm to 10 mm, or more preferably, 2 mm to 6 mm. A width W1 of the rib portion 4 of at least 1 mm, is preferred to ensure stable manufacture with the manufacture method employed. A width W1 of 10 mm or less is preferred to ensure that the rib portions 4 do not become so wide that, although the engagement strength increases, it is hard to peel off the male member.

A width W2 of each groove portion 5 is preferably 0.5 mm to 5 mm. A width of the groove portion 5 of 5 mm or less ensures that it is not too easy for the male member to come off while the absorbent article is being worn.

Figure 13:
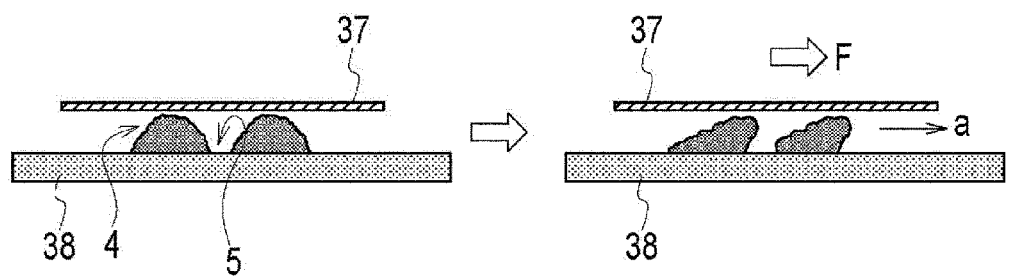
FIG. 13 is a schematic diagram illustrating how the female member of the embodiment of the present invention and a male member engage with each other.
Figure 13:
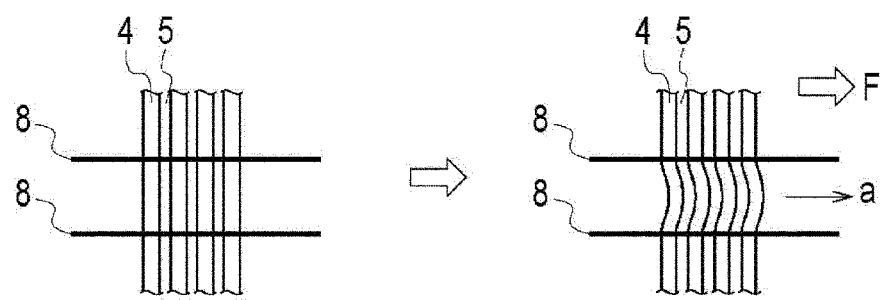

A height H1 of each rib portion 4 (see FIG. 1), namely the thickness of the nonwoven fabric, is preferably 0.2 mm to 5 mm. A height H1 of at least 0.2 mm is preferred to ensure that the male member is not caught by the female member 1 poorly, and to ensure that the effect of elastic deformation of the rib portions 4 (see FIG. 13) is obtained. A height H1 of 5 mm or less is preferred to ensure that the female member 1 does not become more bulky than necessary, and is easy to handle.

Compound fibers having a core-in-sheath structure are selected as the fibrous materials of the nonwoven fabric for the female member 1. The compound fibers has a structure in which a resin constituting sheath components has a lower melting point than a resin constituting core components. The compounding ratio of these resins is preferably 50% or more, or more preferably, 100%. Note that mixing other fibers whose melting point is higher than the sheath components causes a decrease in the overall strength of the nonwoven fabric and falling out of the fibers, and is therefore not preferable. However, it is possible to mix, for example, crimpy fibers to make the fabric bulky, or to mix flexible, elastic threads to complement elastic deformation of the rib portions 4.

Examples of core-component/sheath-component compositions for the fibrous materials include PP (polypropylene)/PE(polyethylene), PP/low-melting PP, PET (polyethylene terephthalate)/low-melting PET, and PET/PE, but the compositions are not limited to these. Fibers that are well compatible with the resin constituting the sheath components of the fibrous materials are selected to be mixed into the fibrous materials. For example, fiber such as acryl, urethane, cotton and polyamide like rayon, PET, PP or nylon, can be selected. Moreover, the fibers are not limited to the above, and any material can be selected as long as a web can be formed by mixing the material into the fibrous materials.

The size of each fibrous material is preferably 1 to 15 dtex, or more preferably, 1.5 to 9 dtex. A size of 1 dtex or more is preferred to ensure the strength of a single yarn is sufficient to not make it easy for the fibers to break when the female member 1 is in engagement with the male member. Moreover, it is easier to form a web using a carding machine and the productivity is increased. A size of 15 dtex or less is preferred to ensure the texture does not deteriorate. Also, since the number of fibers per unit weight may be maintained, it can be ensures that the strength of engagement with the male member does not decrease undesirably.

The length of each fibrous material used is preferably 25 mm to 100 mm, or more preferably, 30 mm to 60 mm. A length of more than 25 mm is preferred to ensure that the fibers are not too short and that fluff is not generated. A length of 100 mm or less is preferred to ensure that it is easy to form a web using a carding machine, thereby increasing the productivity.

In the female member 1 having the above structure, since the fibrous materials of the groove portions 5 are added to the rib portions 4 (the fiber dense portions 2), the rib portions 4 have many fibrous materials and are bulky. As a result, the female member 1 has a good engageability with the male member. Moreover, being formed by the fibrous materials in the groove portions 5 blown by an air jet, the fibrous materials constituting the rib portions 4 are randomly oriented in the MD direction, the CD direction, and also the thickness direction.

In the female member 1 of the hook-and-loop fastener, the pressed portions 8 moderately press the rib portions 4 (the fiber dense portions 2) and the groove portions 5 (the fiber sparse portions 3). Fluff is reduced by forming an embossed pattern intersecting the rib portions 4 and the groove portions 5. Further, since the fibers of the rib portions 4 are moderately pulled when the male member is peeled off, the hook-and-loop fastener can endure an instantaneous peeling force received when the absorbent article is being worn. Also, since the female member 1 and the male member are not attached unnecessarily strongly, the male member can be peeled off easily for intended re-attachment, and fluff can be reduced.

As a result, the female member 1 of the hook-and-loop fastener has large engagement persistence, a good engageability, and less fluff. In contrast, although the fluff may be reduced, a known structure in which fibrous materials are connected to one another by thermal fusion bonding has low engagement persistence and thus a low engageability.

Figure 4:
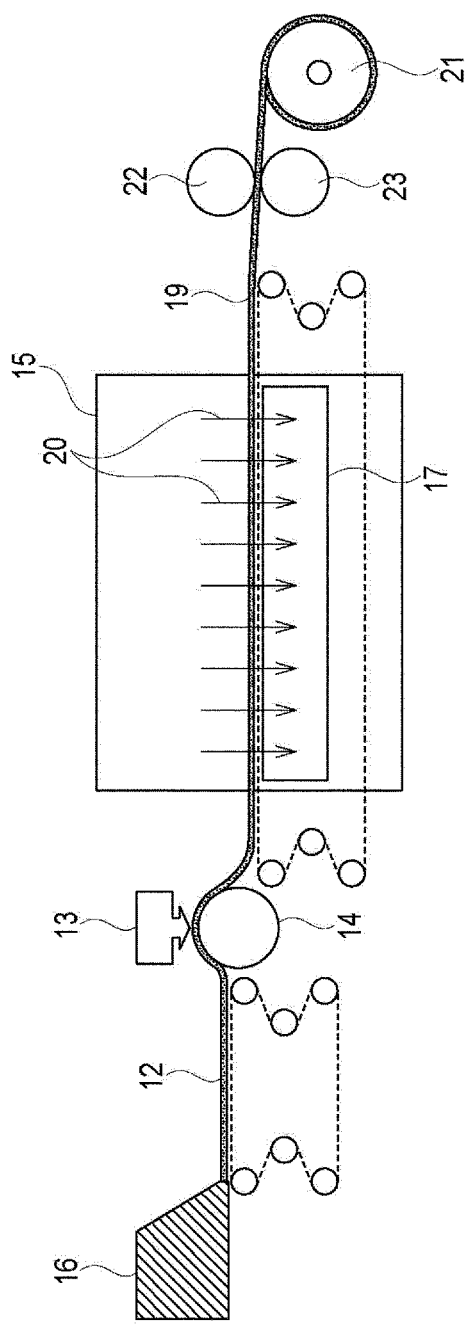
FIG. 4 is a side view of a manufacturing apparatus for manufacturing the female member.

In FIG. 4, reference numeral 12 denotes a fiber web which is a raw material for the female member 1. In a path along which the fiber web 12 is fed, (i) a set of a hot-air jet nozzle 13 and (ii) a perforated plate drum 14, and (ii) a hot-air furnace 15 are placed from the upstream side to the downstream side in this order. A suction device 17 is provided in the hot air furnace 15.

Figure 5:
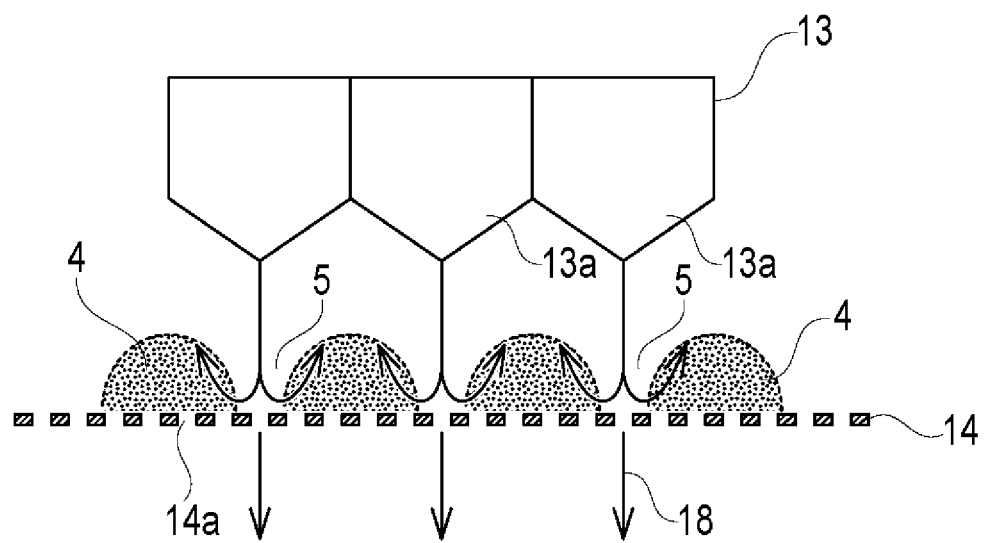
FIG. 5 is a cross-sectional view of a hot-air jet nozzle part of the manufacturing apparatus in FIG. 4.
Figure 6:
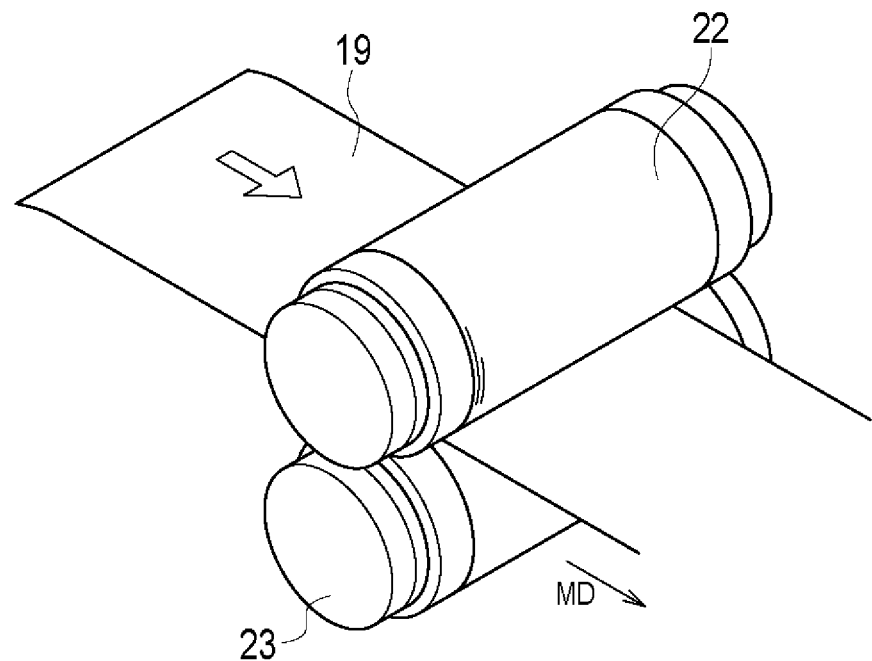
FIG. 6 is a perspective view showing a structure of embossing rollers.

Reference numeral 16 denotes a carding machine that forms the fiber web 12. After being formed by a regular method using the carding machine 16, the fiber web 12 is brought to contact with the perforated plate drum 14. As FIG. 5 shows, the perforated plate drum 14 has many hole portions 14a through which the fiber web 12 is sucked in a direction shown by arrows 18. The hot-air jet nozzle 13 is located above the perforated plate drum 14, and sprays the fiber web 12 with a jet of hot air through its multiple nozzles 13a arranged in the CD direction at a predetermined pitch. A jet of hot air is sprayed through the nozzles 13a on an upper side of the fiber web 12 while a bottom side of the fiber web 12 is being sucked by the perforated plate drum 14. Here, the jet of hot air is +50 deg. C. to −50 deg. C. of the melting point of the fibrous materials.

Some of the fibrous materials blown by the jet of hot air are removed to both sides, and the groove portions 5 are formed in parts after the removal. The removed fibrous materials are laminated like a semi-cylinder between adjacent nozzles 13a, and thereby, the rib portions 4 are formed.

The fiber web 12 passes under the hot-air jet nozzle 13 where the rib portions 4 and the groove portions 5 are formed in the above manner, and the fiber web 12 is then fed as a processed web 19. The processed web 19 is led to the hot-air furnace 15 with the fibrous materials being fused incompletely, and is sprayed with 130 deg. C. to 150 deg. C. hot air 20, as a general air-through nonwoven fabric is. Thus, the fibrous materials are fused completely.

The apparatus for manufacturing the female member 1 includes embossing rollers 22, 23 for performing a press process on the processed web 19 to form the pressed portions 81, 82 thereon. The pressed portions 81, 82 are called an embossed pattern. The embossed pattern can be formed by general embossing rollers. While passing between the embossing rollers 22, 23, the processed web 19 is pressed by the embossing rollers 22, 23. Thereby, a predetermined embossed pattern is formed on the processed web 19.

The embossed pattern only has to be provided to at least one of the embossing rollers 22, 23. In addition, when different embossed patterns are to be formed on the top and the back like the present embodiment, embossing rollers 22, 23 having respective different patterns formed thereon are used.

In the press process by the embossing rollers 22, 23, the embossed pattern can be formed on the processed web 19 by performing a thermal process of 70 deg. C. to 130 deg. C. while pressing the processed web 19. Conditions for the press process is not limited to those described above, and are modifiable. For example, the pressure of the rollers for pressing the processed web 19 can be increased, thereby allowing the process temperature to be reduced.

For example, the embossing rollers 22, 23 have the following structure: the difference in height between a convex portion and a concave portion of the embossed pattern is 2 mm; the line width of the convex portion is 0.9 mm; the temperature of the rollers is 110 deg. C.; and the pressure between the rollers is 1 MPa. The space between the embossing rollers 22, 23 is preferably 0 mm.

The processed web 19 is rolled up by a roll 21 after being subjected to the press process by the embossing rollers 22, 23. However, the roll 21 does not necessarily have to be provided. If the apparatus shown in FIG. 4 is installed in the middle of a manufacturing line for absorbent articles, the apparatus includes, instead of the roll 21, a structure for feeding the processed web 19 to the next step.

Figure 7:
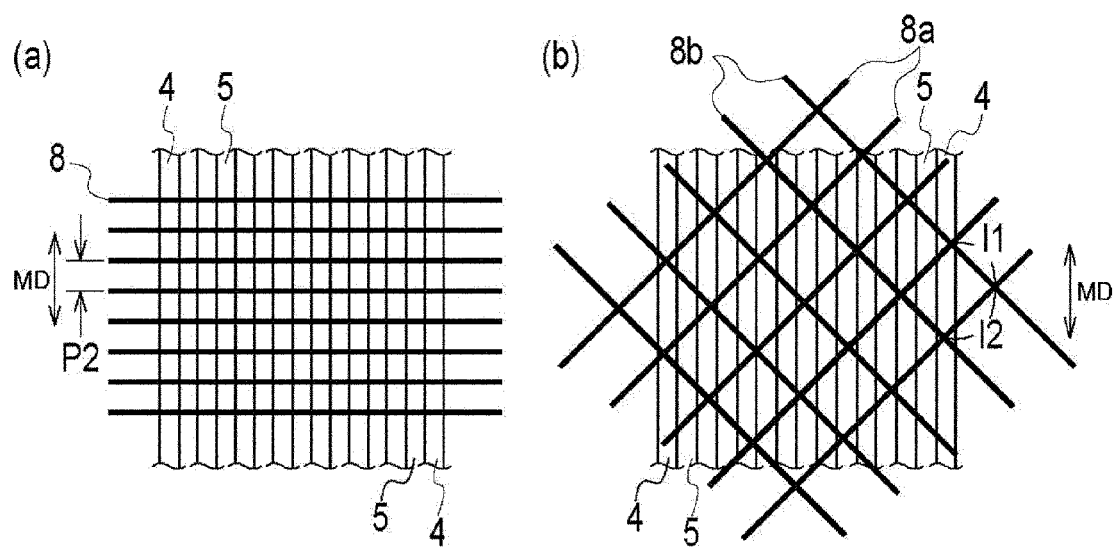
FIGS. 7A and 7B are views each illustrating an embossed pattern formed on a processed web by the embossing rollers.

FIG. 7 is a diagram illustrating an example of the embossed pattern formed on the processed web 19. In the embossed pattern shown in FIG. 7A, pressed portions 8 are each continuous in the CD direction orthogonal to the MD direction of the processed web 19. The pressed portions 8 are formed on the processed web 19 at equal spaces. In the embossed pattern shown in FIG. 7A, an embossing pitch P2 (corresponding to the interline pitch P1) is, as an example, 4 to 15 mm.

FIG. 7B is a diagram illustrating another example of the embossed pattern formed on the processed web 19. In the embossed pattern shown in FIG. 7B, pressed portions 8a are each continuous in a direction intersecting the MD direction of the processed web 19. Further, pressed portions 8b each continuous in a direction orthogonal to the pressed portions 8a are formed. The pressed portions 8a, 8b are formed in grids on the processed web 19. In the embossed pattern shown in FIG. 7B, one side 11 of each grid and another side 12 of the grid are preferably 5 to 15 mm.

The embossed pattern is not limited to those illustrated in FIGS. 7A and 7B. For example, the embossed pattern may have curved lines. Moreover, although the embossed pattern is illustrated as being formed in continuous lines in FIGS. 7A and 7B, the embossed pattern may not necessarily be continuous lines. The embossed pattern may be dot patterns, picture patterns, or the like as long as the pressed portions are formed to press the rib portions 4.

Figure 8:
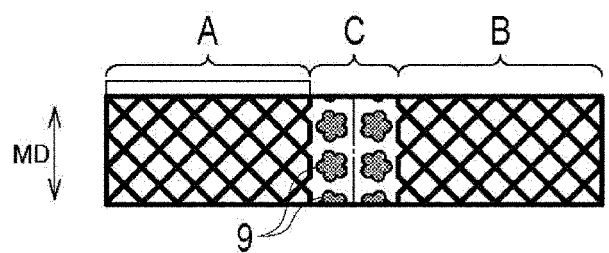
FIG. 8 is a schematic view illustrating an embossed pattern formed on a processed web by embossing rollers.

In addition, the embossed pattern only has to be formed on at least both edge portions in a longitudinal direction of the female member 1. In a modification shown in FIG. 8, instead of the embossed pattern, a marker 9 which indicates the center part of the female member 1 is formed in a center portion C of the female member 1 (corresponding to a female member 38 in FIG. 10 to be described later), which is an area other than both edge portions A, B in the longitudinal direction.

The marker 9 may be part of the embossed pattern. Moreover, a design may be adopted in which patterns printed under the female member 1 appear transparently through the material of the female member 1. The marker 9 preferably has a shape which improves the appearance, such as flowers for example. The marker 9 provided at a position corresponding to the center portion of the female member 1 allows easy positioning of the male member and the female member. This prevents out-of-alignment attachment of the male member to the female member.

In the above manufacturing apparatus, the rib portions 4 and the groove portions 5 can be formed on both sides of the web by shaping wave shapes in synchronization with the hot-air jet nozzle 13 in the CD direction of the perforated plate drum 14. Further, in a case where the opening portions 6 (see FIGS. 2 and 3) are to be formed in the groove portions 5, portions having no hole portions 14a are provided at a predetermined interval on the lines, on the perforated plate drum 14, sprayed with a jet of hot air. Thus, the opening portions 6 can be formed in the portions having no hole portions 14a.

Figure 9:
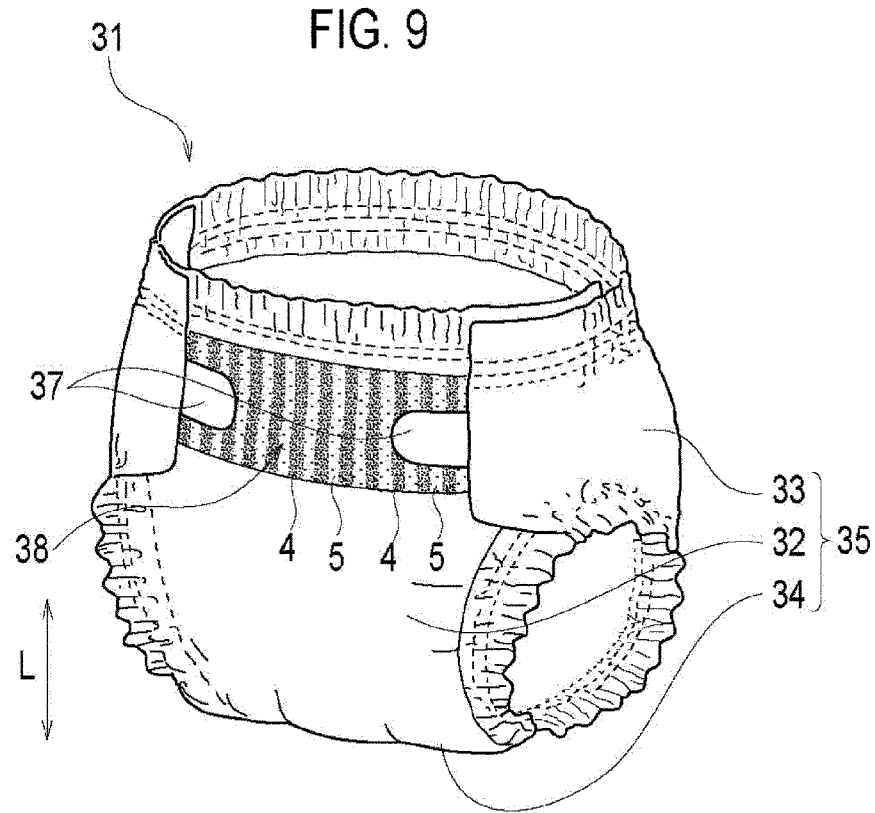
FIG. 9 is a perspective view showing an embodiment of an absorbent article of the present invention.

FIG. 9 shows an embodiment example of an absorbent article 31 employing the hook-and-loop fastener according to the embodiment of the present invention. The absorbent article 31 is a so-called open-type disposable diaper, in which an outer member 35 is formed by a front waistline portion 32, a back waistline portion 33, and a crotch portion 34 therebetween. An absorber (not shown in FIG. 9) is integrally provided in the crotch portion 34. A permeable topsheet is placed on the skin facing side of the absorber. The outer member 35 is liquid impermeable.

The back waistline portion 33 is overlapped on the front waistline portion 32 at both widthwise edge portions. Male members 37 are attached to both the respective widthwise edge portions of the back waistline portion 33. As a counterpart member, a female member 38 is provided to an upper outer surface of the front waistline portion 32. The female member 38 is shaped as a belt extending in the width direction. The fiber dense portions 2 (the rib portions 4) and the fiber sparse portions 3 (the groove portions 5) of the female member 38 are each continuous in a longitudinal direction L of the absorbent article 31. The longitudinal direction of the absorbent article 31 is a vertical direction when the absorbent article 31 is being worn. The diaper is used by engaging the male members 37 with the female member 38. The female member 38 may be provided covering the entire front waistline portion 32.

Excellent engagement between the female member 38 and the male members 37 can be obtained by using the female member 1 shown in FIGS. 1 to 3 as the female member 38 of the absorbent article 31. Accordingly, the female member 38 and the male members 37 do not disengage from each other even when the diaper changes in shape or receives an instantaneous impulsive force.

In particular, the rib portions 4 and the groove portions 5 of the female member 38 in the absorbent article 31 are each continuous in the longitudinal direction L of the absorbent article 31. This causes the fibers of the rib portions 4 to be pulled moderately even upon receipt of a peeling force in a waistline direction, and the female member 38 can thus endure such instantaneous peeling force received by the absorbent article 31. In addition, to intentionally re-attach the male members 37, the male members 37 can easily be peeled off, preventing generation of fluff due to repeated attachment and detachment.

Figure 10:
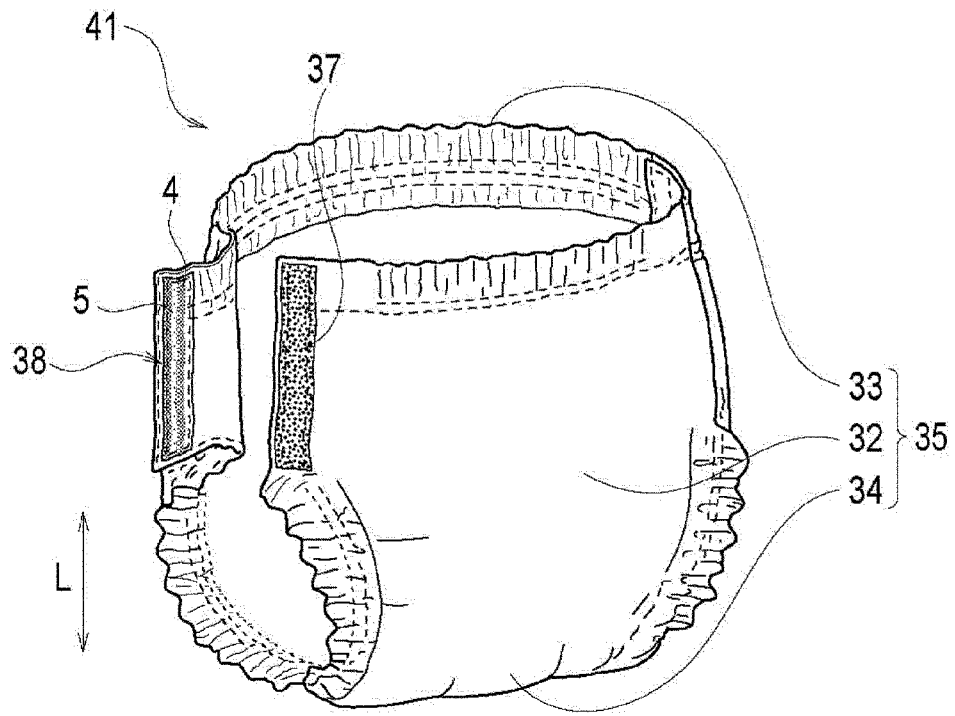
FIG. 10 is a perspective view showing a release state of a hook-and-loop fastener.

FIG. 10 shows another absorbent article, an absorbent article 41, and corresponds to FIG. 9 by having the same reference numerals for the same members. The front waistline portion 32 and the back waistline portion 33 are provided with hook-and-loop fasteners each including a female member and a male member, in the width direction. The absorbent article 41 functions as a pants-type diaper by engaging the female member and the male member of each of the hook-and-loop fasteners with each other.

The male member 37 is provided to each of outer-surface edge portions of the front waistline portion 32. In addition, a female member 38 is provided to each of inner-surface edge portions of the back waistline portion 33. The absorbent article 41 keeps its pants-type form by engagement between the female member 38 and the male member 37. The fiber dense portions 2 (the rib portions 4) and the fiber sparse portions 3 (the groove portions 5) of the female member 38 are each continuous in the longitudinal direction L of the absorbent article 41. In this absorbent article 41, too, unexpected disengagement of the male member 37 can be prevented by using the female member 1 shown in FIGS. 1 to 3 as the female member 38.

Further, the female member 38 is moderately pulled when a peeling force is received in the waistline direction, and therefore can endure an instantaneous peeling force received by the absorbent article 41. Further, to intentionally re-attach the male member 37, the male member 37 can be easily peeled off, preventing generation of fluff due to repeated attachment and detachment.

Moreover, in the absorbent article 41 having such structure, the female member 38 is located on the wearer's body side. Since the female member 38 is located there, the wearer is not damaged. This is because the female member 38 has the rib portions 4 and the groove portions 5 and is soft and excellent in breathability. The topsheet of the absorbent article 31, 41 and the female member 1 can be formed of the same material.

To use a nonwoven fabric forming the female member 1 as the topsheet of the absorbent article 31, 41, it is preferable that the multiple lines of the fiber dense portions 2 (the rib portions 4) and the multiple lines of the fiber sparse portions 3 (the groove portions 5) of the female member 1 be aligned with the longitudinal direction L of the absorbent article 31, 41. The topsheet has the rib portions 4 and the groove portions 5 formed thereon. Accordingly, when the female member 1 is used as a topsheet, at least the rib portions 4 is in contact with the skin of the wearer, and a space is formed between the groove portions 5 and the skin. Thus, the groove portions 5 function as ventilation paths extending in the longitudinal direction L, allowing moisture in the absorbent article to be discharged to the outside of the absorbent article through the groove portions 5.

Moreover, since at least the rib portions 4 is in contact with the skin of the wearer, and a space is formed between the groove portions 5 and the skin, an area in contact with the skin can be reduced, compared to that in a conventional topsheet in which the entire topsheet is in contact with the skin. Consequently, skin troubles due to rubbing of the skin by the topsheet can be reduced.

Then a nonwoven fabric forming the female member 1 is to be used as the topsheet of the absorbent article 31, 41, the topsheet and the absorber are bonded to each other with a bonding material (also referred to herein as a first bonding material) such as a hot-melt bonding material. The bonding material extends in the longitudinal direction of the topsheet of the absorbent article 31, 41, and can be formed in multiple lines spaced from one another in the width direction. A bonding material application width W3 (see FIG. 11) is preferably smaller than the width W1 of the rib portion 4. Further, an application pitch P3 of the bonding material in the width direction is larger than the interline pitch P1 of the rib portions 4. Or, a widthwise space distance between each adjacent pair of lines of the bonding material is preferably larger than the width of the rib portion 4. For example, when the width W1 of the rib portion 4 is 3 mm and the width W2 of the groove portion 5 is 1 mm, the application width W3 of a hot-melt bonding material is set to 0.5 mm, and the application pitch P3 is set to 5 mm.

Body fluid such as urine is absorbed after contacting the rib portions 4. Body fluid such as urine absorbed into the rib portions 4 is difficult to move further into the absorber if the bonding material overlaps the rib portions 4; therefore, the bonding material is preferably arranged to avoid the rib portions 4. Note that an absorbable sheet formed of tissue or the like may be interposed between the topsheet and the absorber.

In the above embodiment, the female member 38 is used as part of the absorbent article 31, 41 as a disposable diaper. Note, however, that at least one of the front waistline portion 32 and the back waistline portion 33 may be formed entirely of the female member 38. In addition, in the above embodiment, the absorbent article is described as being a disposable diaper whose outer member has the front waistline portion and the back waistline portion that are continuous to the crotch portion. Alternatively, the absorbent article may be of a type in which a front waistline portion, a back waistline portion, and a crotch portion are formed as separate members and are integrally attached to each other.

Figure 11:
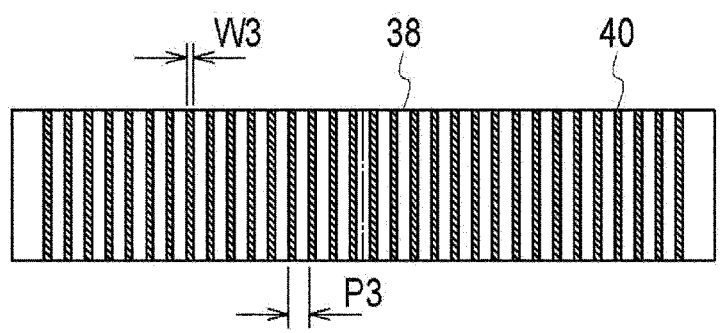
FIG. 11 is a diagram illustrating where a hot-melt bonding material is applied to attach the female member to the absorbent article.
Figure 12:
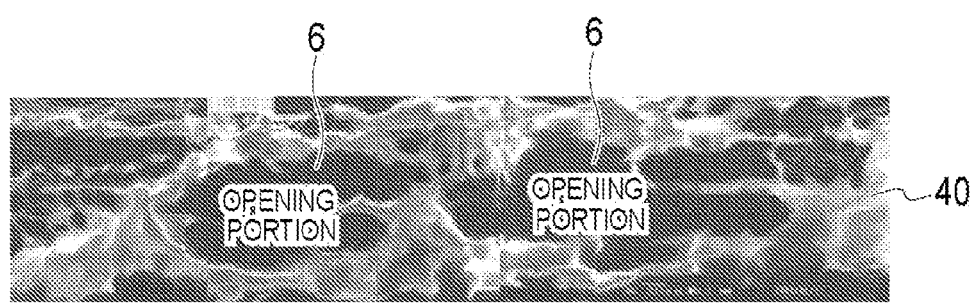
FIG. 12 is a diagram illustrating how the hot-melt bonding material is applied near opening portions.

Next, using FIGS. 11, 12, a method for attaching the female member 38 to the absorbent article 31, 41 is described. Here, a method for attaching the female member 38 and the absorbent article 41 shown in FIG. 10 to each other is described. FIG. 11 is a diagram illustrating an application pattern of a hot-melt bonding material 40 on the female member 38. The hot-melt bonding material 40 is applied in lines which are along the MD direction and parallel with the rib portions 4 and the groove portions 5. A coater or the like is used to apply the hot-melt bonding material.

In the preset embodiment, the hot-melt bonding material 40 (corresponding to a second bonding material) is applied between a back side of the female member 38 and the absorbent article 31, 41. Here, the back side is opposite to a side where the rib portions 4 are formed. Further, in the present embodiment, the hot-melt bonding material 40 is applied in an area 50% or more of an area corresponding to the width W1 of the rib portion 4. This allows enough adhesion to be obtained between the female member 38 and the absorbent article 31, 41.

It is preferred that the application area of the hot-melt bonding material 40 on the back side of the female member 38 is at least 50% of the area corresponding to the width W1 of the rib portion 4, to ensure enough adhesion can be obtained, making it unlikely that the female member 38 comes off from the absorbent article 31, 41 together with the male member 37 when the male member 37 is to be peeled off from the female member 38.

In the present embodiment, the application width W3 of the hot-melt bonding material is preferably 0.5 mm or more, and more preferably, 1 mm or more. In the example shown in FIG. 11, W3 is 1.0 mm. It is preferred that W3 is at least 0.5 mm, to ensure that the adhesion is strong, preventing the hook-and-loop fastener to come off from the product upon receipt of a shearing and peeling force. For example, when the width W1 of the rib portion 4 is 3 mm, and the width W2 of the groove portion 5 is 1.5 mm, the hot-melt bonding material 40 is applied on the female member 38 with the application width W3 of 3 mm and a distance to an adjacent application portion (a space distance) of 1.5 mm (in other words, the application pitch P3 of 4.5 mm).

Here, the application width W3 of the hot-melt bonding material 40 is the same as the width W1 of the rib portion 4. In this case, it is preferable that the application pitch P3 of the hot-melt bonding material 40 be almost the same as the interline pitch P1 of the rib portions 4 and the groove portions 5 because then the hot-melt bonding material 40 is always applied under the rib portion 4. However, considering shifts of the application positions of the hot-melt bonding material in actual manufacturing, the application pitch P3 of the hot-melt bonding material 40 may be set slightly larger than the interline pitch P1 of the rib portions 4 and the groove portions 5.

In contrast, if the application pitch P3 of the hot-melt bonding material 40 is much wider than the pitch P1 of the ribs and grooves, the hot-melt bonding material 40 is not applied under some of the rib portions 4. In this case, a stress is concentrated in the rib portions 4 under which the hot-melt bonding material 40 is applied and which are adjacent to the rib portions 4 under which the hot-melt bonding material 40 is not applied. This stress concentration may cause the female member 38 to come off from the absorbent article 41. Once the female member 38 comes off at one portion, the rib portions 4 adjacent to the stress concentration location are sequentially influenced, causing the female member 38 to come off at another portion and then another portion. This is why the application pitch P3 of the hot-melt bonding material 40 is preferably almost the same as or less than the interline pitch P1 of the rib portions 4 and the groove portions 5. Assume, for example, that the interline pitch P1 is 4 mm and the application pitch P3 is 4.5 mm. Reducing the application pitch P3 too much without changing the application width W3 reduces the widthwise space distance between each adjacent pair of the hot-melt bonding material 40. This increases the amount of the hot-melt bonding material to be used, and is thus not economical. In addition, it is likely that the female member 38 and the absorbent article 31, 41 are attached to each other with the female member 38 having wrinkles.

When the application width W3 of the hot-melt bonding material 40 is 50% or more of the width W1 of the rib portion 4, and is smaller than the width W1 of the rib portion 4, the amount of the hot-melt bonding material 40 to be used can be reduced, offering an economical advantage.

Moreover, if the opening portions 6 are to be formed in the groove portions 5 (the fiber sparse portions 3), the application width W3 of the hot-melt bonding material 40 is set larger than the width W2 of the groove portion 5. Because the application width W3 of the hot-melt bonding material 40 is larger than the width W2 of the groove portion 5, even when the hot-melt bonding material 40 is shifted in application position and applied under the groove portion 5, a hot-melt bonding material out of an area under the groove is applied under the rib portion 4. Further, if the hot-melt bonding material 40 is applied using means such as a coater that directly contacts the web, the hot-melt bonding material 40 is applied not under the opening portions 6, but under the rib portions 4 and the groove portions 5 provided with no opening portions 6.

FIG. 12 is a diagram illustrating how the hot-melt bonding material 40 is actually applied, by coater application, on a surface of the female member 1 (the rib portions 4 and the groove portions 5). The hot-melt bonding material 40 is applied avoiding the opening portions 6.

Next, a description is given of how the female member of the present embodiment and the male member engage with each other. As an example, the description is given using the female member 38 and the male member 37 of FIG. 10. FIG. 13A is cross-sectional views showing how the female member 38 and the male member 37 engage with each other. FIG. 13B is top views of the female member 38. Note that the male member 37 is not illustrated in FIG. 13B for clear illustration.

For example, when the female member 38 is bent or receives an instantaneous force (an impulsive peeling force: arrow F in the drawings) by the movement or the abdominal pressure of the wearer, elastic deformation occurs, in which top portions of the rib portions 4 are pulled in a direction shown by arrow a, and the width of each rib portion 4 is reduced in the direction shown by arrow a. Such elastic deformation of the rib portions 4 allows the impulsive peeling force to be absorbed.

Further, since the rib portions 4 are pressed by the pressed portions 8 obtained by the embossing process, the rib portions 4 change shape from lines where the rib portions 4 intersect the pressed portions 8, and curve toward the peeling direction shown by arrow a to be a convex shape. Thereby, the impulsive peeling force can be further absorbed.

EXAMPLES

Manufacturing Method

A female member (a nonwoven fabric) of a hook-and-loop fastener was manufactured by supplying fibers having a compounding ratio shown in Table 1 to the manufacturing apparatus shown in FIGS. 4 and 5. The female member is manufactured as follows. The hot-air jet nozzle 13 having four nozzles 13a sprayed a jet of 150 deg. C. hot air with an air volume of 0.12 m$^3$/minute/m$^2$. Here, the four nozzles 13a were each with a hole diameter of 1.0 mm and were arranged at a 50-mm pitch. Thereafter, the 150 deg. C. hot air 20 having an air volume of 15 m$^3$/minute/m$^2$ was sprayed for about 10 seconds in the hot-air furnace 15. Thereby an air-through nonwoven fabric of Example 1 was obtained, which had a rib-and-groove structure in which the basis weight was 27 g/m$^2$, a pitch of the rib portions 4 was 4 mm, and the width of each groove portion 5 was 1.1 mm. In this case, the opening portions 6 were formed in the groove portions 5 in the MD direction at a 5-mm pitch.

Meanwhile, air-through nonwoven fabrics of Comparative Examples 1 to 3 were manufactured at a compounding ratio described later (in Table 1) with the same conditions as Example 1 except for the following points. Specifically, the nonwoven fabric of Comparative Example 1 was manufactured by changing the condition of the air volume of the jet of hot air in Example 1 to 10 m$^3$/minute/m$^2$. In Comparative Example 2, the process of spraying a jet of hot air from hot-air jet nozzle 13 was not performed, but an embossing process was performed. Moreover, in Comparative Example 3, neither the hot-air jet process nor the embossing process was performed.

(Evaluation)

The nonwoven fabrics of Embodiment 1 and Comparative Examples 1 to 3 were engaged in the MD direction with respective male members having the same structure, and were evaluated in terms of peeling strength, fluff generation, retention strength, and engagement persistency. The basis weight, the thickness, and the like of a test piece used are shown in Table 1.

TABLE 1

| | FIBROUS MATERIAL AND COMPOUNDING RATIO | BASIS WEIGHT (g/m²) | RIB AND GROOVE | EMBOSS | THICKNESS (mm) |
|---|---|---|---|---|---|
| EXAMPLE | PET/PE | 27 | YES | YES | 0.7 |
| COMPARATIVE EXAMPLE 1 | 2.2 dtex × 45 mm 80% | | YES | NO | 0.7 |
| COMPARATIVE EXAMPLE 2 | 2.6 dtex × 38 mm 20% | | NO | YES | 0.6 |
| COMPARATIVE EXAMPLE 3 | | | NO | NO | 0.6 |

An evaluation method is described below.

(Thickness Measurement)

A 10-cm square sample was measured by using a thickness gauge (product name: PEACOCK DIAL THICKNESS GAUGE No. CI1352) under a load of 3 g/cm². (135 deg.-peeling Test)

Each of the nonwoven fabrics manufactured as the female member was cut into a test piece of 3 cm to 5 cm×5 cm. Using a double-sided adhesive tape, the test piece was undetachably attached on a 5 cm×8 cm spunbond nonwoven fabric (20 to 30 g/cm²), to thereby obtain a female member sample 53. Meanwhile, using a double-sided adhesive tape, a 2 cm×3 cm male member was undetachably attached on a 12 cm×3 cm spunbond nonwoven fabric (20 to 30 g/cm²), to thereby obtain a male member sample 56.

Using a double-sided adhesive tape, the female member sample 53 was attached on a 6 cm×10 cm stainless plate with the female member 53 having no wrinkles. Then, the male member sample 56 is laminated on the female member sample 53, and the test piece (the female member) and the male member were brought to engagement by reciprocating a 700-g roller thereon once at a rate of 300 mm/min. Then, to exert a shearing force on the engagement interface, a 500-g load was put for three seconds from one edge of the male member sample 56 engaging with the female member 53. Note that the roller had a 45-mm width and a 95-mm diameter, and a tape press-bonding roller used was of TESTER SANGYO CO., LTD.

Figure 14:
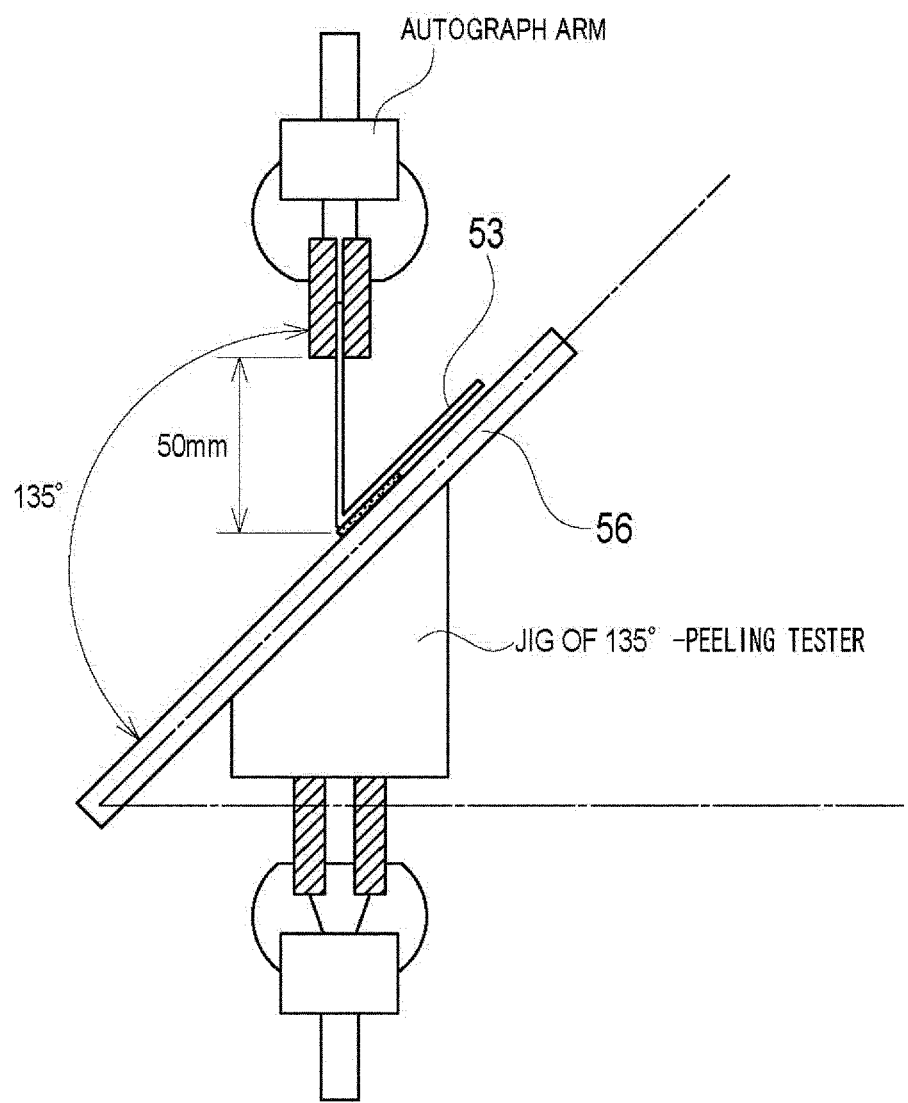
FIG. 14 is a front view of a 135 deg.-peeling tester.

FIG. 14 shows a 135 deg.-peeling tester, in which the above-mentioned stainless plate was fixed to an autograph, and the male member sample 56 is pulled from one edge thereof at a 135 deg. peeling angle between the male member sample 56 and the female member sample 53, and is thus peeled off. Here, a force necessary for this peeling is set to be a 135 deg.-peeling force.

Conditions for the autograph were set as follows.

Measurement Conditions: a load cell=5 kg, a peeling rate=300 mm/min, and a (vertical) distance between an upper chuck and the sample=50 mm (Retention Strength Test)

A female member sample 59 used for a retention strength test is fabricated by undetachably attaching a 5 cm×5 cm female member 61 to a 10 cm×10 cm spunbond nonwoven fabric (20 to 30 g/cm²) using a double-sided adhesive tape. Further, a male member sample used for the retention strength test was fabricated by undetachably attaching a 2 cm×4 cm male member 54 to a 4 cm×8 cm spunbond nonwoven fabric (20 to 30 g/cm²) using a double-sided adhesive tape.

The male member sample thus fabricated was laminated on the female member sample 59, and the male member 54 and the female member 61 were brought to engagement by reciprocating a 700-g roller thereon once at a rate of 300 mm/min. Then, these samples were let stand for 30 minutes under 20 deg. C. and 60% RH.

Figure 15:
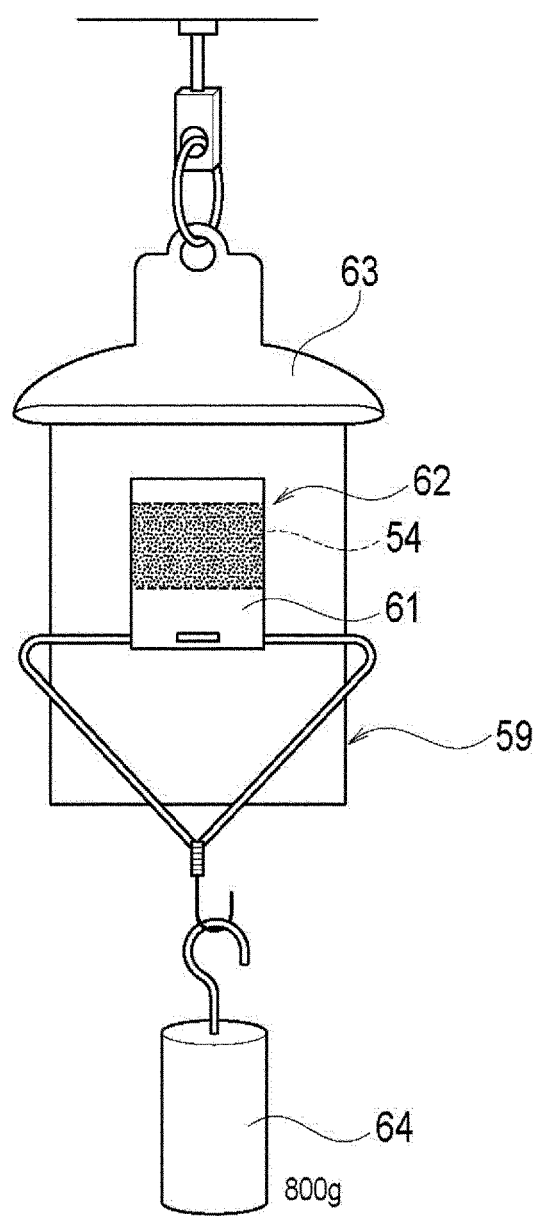
FIG. 15 is a front view of a retention strength tester.

FIG. 15 is a retention strength tester, in which the female member sample 59 was hung at its upper edge portion by a fastening device 63, and an 800-g weight 64 was hung on a lower edge portion of the male member sample 62. Then these samples were let stand in a 40 deg. C. atmosphere. Then, a time taken for the weight 64 to fall due to disengagement was measured as a retention strength. In this case, if the weight 64 did not fall even after 60 minutes, the sample was measured as having the maximum retention strength, which is 60 minutes.

(Peeling Test (Shearing Direction))

A female member sample used for a peeling test was fabricated by undetachably attaching a 4 cm×4 cm female member to a 5 cm×5 cm spunbond nonwoven fabric (20 to 30 g/cm²) using a double-sided adhesive tape. A 2 cm×3 cm male member used for an engagement persistency test was attached to a back side of a 2 cm×8 cm spunbond nonwoven fabric (50 to 80 g/cm²) using a double-sided adhesive tape. Then, the male member was laminated on a female member sample, and the male member and the female member were brought to engagement by reciprocating a 700-g roller thereon once at a rate of 300 mm/min.

Figure 16:
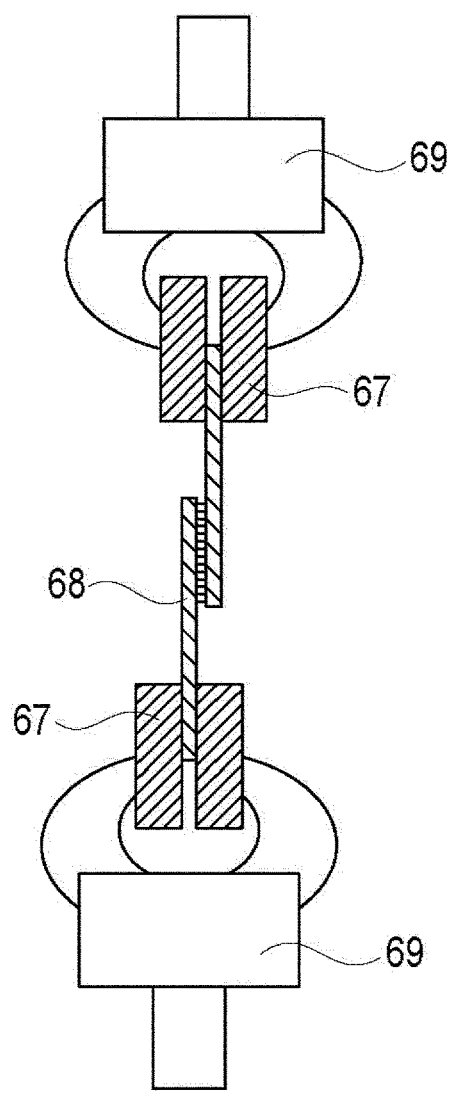
FIG. 16 is a front view showing a peeling tester.

FIG. 16 is a peeling tester used for a test for peeling in a shearing direction, in which a sample 68 having the male member and the female member engaging with each other was interposed between upper and lower clamps 67. Next, the upper and lower clamps 67 were fixed to upper and lower autographs 69, respectively, and an engagement strength in the shearing direction was measured.

Conditions for the autographs were set as follows.

Measurement Conditions: a load cell=5 kg, and a peeling rate=10 mm/min

Table 2 shows evaluation results obtained by the above-described evaluation method.

TABLE 2

| | PEELING STRENGTH 135° PEEL(N) | | | | | RETENTION STRENGTH | SHEARING | |
|---|---|---|---|---|---|---|---|---|
| | 1st time | 2nd time | 3rd time | 4th time | 5th time | (minute) | PEEL | FLUFF |
| EXAMPLE | 1.4 | 1.9 | 1.7 | 1.2 | 1.2 | 81 | ○ | ○ |
| COMPARATIVE EXAMPLE 1 | 1.2 | 1.2 | 1.1 | 0.9 | 0.9 | 81 | Δ | Δ |

TABLE 2-continued

| | PEELING STRENGTH 135° PEEL(N) | | | | | RETENTION STRENGTH | SHEARING | |
|---|---|---|---|---|---|---|---|---|
| | 1st time | 2nd time | 3rd time | 4th time | 5th time | (minute) | PEEL | FLUFF |
| COMPARATIVE EXAMPLE 2 | 2.4 | 2.1 | 1.6 | 1.1 | 0.8 | 26 | ○ | Δ |
| COMPARATIVE EXAMPLE 3 | 1.1 | 1.24 | 0.93 | 0.8 | — | 1 | X | X |

EVALUATION OF FLUFF GENERATION
⊚ NOT FLUFFY
○ LESS FLUFFY
Δ FAIRY FLUFFY
X FLUFFY

As Table 2 shows, the female member of Example 1 obtained good results, for both the top side and the back side, in all of the 135 deg.-peeling test performed 1 to 5 times to measure the peeling strength and fluff generation, the retention strength test, and the engagement persistency test. The female member of Example 1 had a good result in its retention strength.

In contrast, Comparative Example 1 provided a peeling strength and a retention strength comparable to Example 1, but provided poor results in the retention test and the peeling test. Comparative Example 2 had a too strong peeling strength for the first peeling testing of the 135 deg.-peeling test. Further, in the fifth peeling testing, Comparative Example 2 had a poorer result than a result of Example 1 in the first peeling testing. This shows that Comparative Example 2 deteriorates fast in peeling strength as the number of peelings increases, and therefore is not appropriate as a product. Moreover, none of the result values shows that Comparative Example 3 can endure use as a product. Accordingly, Comparative Examples 1 to 3 can be determined as not being qualified to be used as the female member.

Note that the entire contents of the Japanese Patent Application No. 2009-208695, filed on Sep. 9, 2009 is incorporated herein by reference.

REFERENCE SIGNS LIST

1 . . . female member, 2 . . . fiber dense portion, 3 . . . fiber sparse portion, 4 . . . rib portion, 5 . . . groove portion, 6 . . . opening portion, 7 . . . base layer portion, 8a, 8b . . . pressed portions, 9 . . . marker, 21 . . . roll, 22, 23 . . . embossing rollers, 31, 41 . . . absorbent article, 32 . . . front waistline portion, 33 . . . back waistline portion, 34 . . . crotch portion, 35 . . . outer member, 37 . . . male member, 38 . . . female member, 40 . . . hot-melt bonding material, 81, 82 . . . pressed portions

The invention claimed is:

1. An absorbent article formed of an outer member having a front waistline portion, a back waistline portion, and a crotch portion and of an absorber provided integrally to the crotch portion, the absorbent article comprising a hook-and-loop fastener that includes:
a male member which is provided to any one of the front waistline portion and the back waistline portion and which has an engagement surface formed of a group of a plurality of protrusions; and
a female member which is formed of a fibrous material and is configured to engage with the male member, wherein the female member includes:
a plurality of lines of fiber dense portions in which the fibrous material has a high basis weight;
a plurality of lines of fiber sparse portions provided between the plurality of lines of fiber dense portions, the fibrous material in the fiber sparse portions having a basis weight lower than that in the fiber dense portions; and
pressed portions intersecting the plurality of lines of fiber dense portions and the plurality of lines of fiber sparse portions.

2. The absorbent article according to claim 1, wherein
the female member is rectangular and provided to the front waistline portion, and
the pressed portions are formed in at least both lengthwise edge portions of the female member.

3. The absorbent article according to claim 2, wherein a marker indicating a center part of the female member is formed in a center portion of the female member, the center portion being other than both the lengthwise edge portions.

4. The absorbent article according to claim 1, wherein a topsheet of the absorbent article and the female member are formed of a same material.

5. The absorbent article according to claim 4, wherein
a first bonding material is placed between the absorber and the topsheet formed of the same material as the female member, the first bonding material bonding the topsheet to the absorber,
a second bonding material is placed between a back side of the female member, the back side being opposite to a side where the fiber dense portions are formed, and another portion of the absorbent article, the second bonding material bonding the female member to the another absorbent article, and
an application width of the first bonding material is smaller than a width of each of the fiber dense portions formed on the topsheet, and is smaller than an application width of the second bonding material.

6. The absorbent article according to claim 1, wherein the second bonding material is applied on a back side of the female member, in an area 50% or more of an area corresponding to a width of each of the fiber dense portions.

7. The absorbent article according to claim 1, wherein the fiber dense portions and the fiber sparse portions are each continuous in a longitudinal direction of the absorbent article.

8. The absorbent article according to claim 1, wherein the fiber dense portions comprise ribs and the fiber sparse portions comprise grooves, and the fibrous material has a greater thickness at the fiber dense portions than at the fiber sparse portions.

9. The absorbent article according to claim 1, wherein the fiber dense portions are wider than the fiber sparse portions.

10. The absorbent article according to claim 1, wherein the fiber sparse portions and the fiber dense portions are arranged alternately to one another.

11. The absorbent article according to claim 1, wherein opening portions, which penetrate from the front to the back of the female member in the thickness direction, are provided in the fiber sparse portions.

12. The absorbent article according to claim 1, wherein the pressed portions are orthogonal or oblique to the lines of fiber sparse and fiber dense portions.

13. The absorbent article according to claim 1, wherein the pressed portions are narrower than the lines of fiber sparse and fiber dense portions.

14. The absorbent article according to claim 1, wherein the basis weight of the fibrous material is 15 to 100 g/m$^2$.

15. The absorbent article according to claim 1, wherein the pitch between adjacent pairs of ribs is 1.5 to 15 mm, the width of each rib is 1 to 10 mm, the width of each groove is 0.5 to 5 mm and a height of each rib is 0.2 to 5 mm.

* * * * *